US00PP24803P2

(12) United States Plant Patent
Leue

(10) Patent No.: US PP24,803 P2
(45) Date of Patent: Aug. 19, 2014

(54) ***HEUCHERA* PLANT NAMED 'CARNIVAL WATERMELON'**

(50) Latin Name: *Heuchera×hybrida*
Varietal Denomination: Carnival Watermelon

(75) Inventor: Ellen Leue, Dekalb, IL (US)

(73) Assignee: Ball Horticultural Company, West Chicago, IL (US)

( * ) Notice: Subject to any disclaimer, the term of this patent is extended or adjusted under 35 U.S.C. 154(b) by 187 days.

(21) Appl. No.: 13/507,881

(22) Filed: Aug. 3, 2012

(51) Int. Cl.
*A01H 5/00* (2006.01)

(52) U.S. Cl.
USPC ..... Plt./440

(58) Field of Classification Search
CPC ..... A01H 5/02; A01H 5/12
USPC ..... Plt./440
See application file for complete search history.

*Primary Examiner* — June Hwu
(74) *Attorney, Agent, or Firm* — Audrey Charles

(57) ABSTRACT

A new and distinct cultivar of *Heuchera* plant named 'Carnival Watermelon', characterized by its immature foliage color of greyed burgundy-red with a slight silvery overlay and prominent reddish to reddish-brown venation, mature foliage color of greyed green and prominent green venation, and moderately vigorous and mounded growth habit, is disclosed.

1 Drawing Sheet

Latin name of genus and species of plant claimed: *Heuchera×hybrida.*

Variety denomination: 'Carnival Watermelon'.

BACKGROUND OF THE INVENTION

The present invention relates to a new and distinct cultivar of *Heuchera* plant botanically known as *Heuchera×hybrida* and hereinafter referred to by the cultivar name 'Carnival Watermelon'.

The new cultivar originated in a controlled breeding program in Elburn, Ill. during May 2009. The objective of the breeding program was the development of *Heuchera* cultivars with unique foliage coloration and mounded growth habit.

The new *Heuchera* cultivar is the result of cross-pollination. The female (seed) parent of the new cultivar is the proprietary *Heuchera×hybrida* breeding selection coded 222-4, not patented, characterized by its dark purple and silver colored foliage, white-colored flowers, and moderately vigorous, mounded growth habit. The male (pollen) parent of the new cultivar is the proprietary *Heuchera×hybrida* breeding selection coded 222-9, not patented, characterized by its dark brownish-purple and silver colored foliage, light pink-colored flowers, and moderately vigorous, compact-mounded growth habit. The new cultivar was discovered and selected as a single flowering plant within the progeny of the above stated cross-pollination during March 2010 in a controlled environment in Elburn, Ill.

Asexual reproduction of the new cultivar by in vitro propagation since March 2010 in West Chicago, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Carnival Watermelon' as a new and distinct cultivar of *Heuchera* plant:

1. Immature foliage color of greyed burgundy-red with a slight silvery overlay and prominent reddish to reddish-brown venation;
2. Mature foliage color of greyed green and prominent green venation; and
3. Moderately vigorous and mounded growth habit.

Plants of the new cultivar differ from plants of both the female and male parents primarily in having a different foliage color.

Of the many commercially available *Heuchera* cultivars, the most similar in comparison to the new cultivar is 'Peach Flambe', U.S. Plant Pat. No. 17,195. However, in comparison, plants of the new cultivar differ from plants of 'Peach Flambe' in at least the following characteristics:

1. Plants of the new cultivar have a mature foliage color that is different from plants of 'Peach Flambe'; and
2. Plants of the new cultivar have less deeply lobed foliage than plants of 'Peach Flambe'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Carnival Watermelon'. The plants were grown in one-gallon containers for approximately one year in a greenhouse in West Chicago, Ill.

DETAILED BOTANICAL DESCRIPTION

Figure 1:
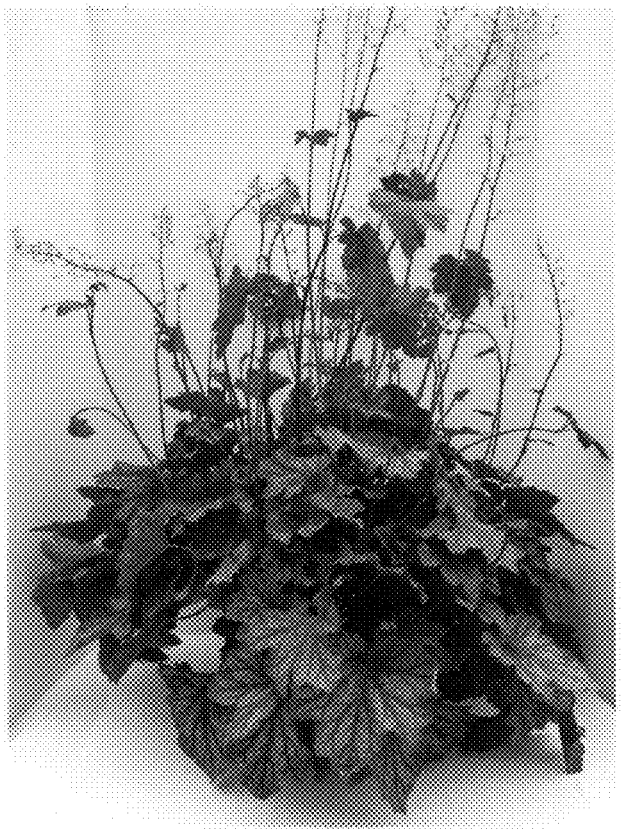
FIG. 1 illustrates a side view of the overall growth habit of 'Carnival Watermelon'.
Figure 2:
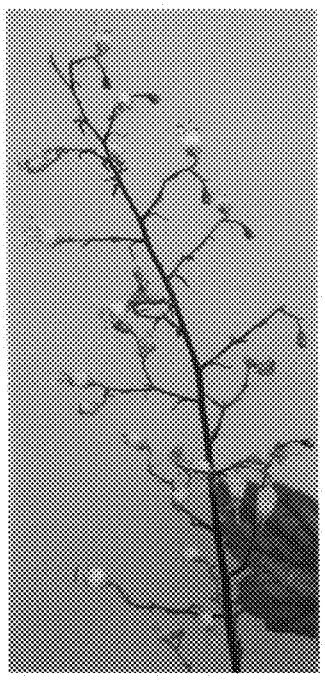
FIG. 2 illustrates a close-up view of an individual inflorescence of 'Carnival Watermelon'.
Figure 3:
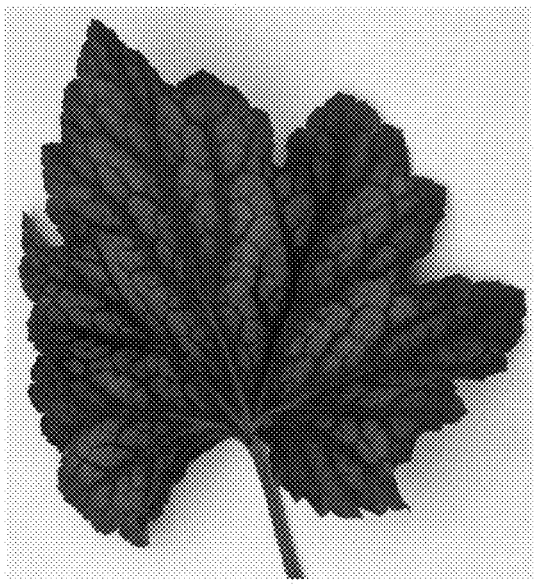
FIG. 3 illustrates a close-up view of an individual leaf of 'Carnival Watermelon'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2007 edition, except where general color terms of ordinary significance are used. The color values were determined in May 2012 under natural light conditions in West Chicago, Ill.

The following descriptions and measurements describe plants produced from in vitro plantlets and grown in a glass-covered greenhouse under conditions comparable to those used in commercial practice. The plants were grown in West Chicago, Ill. in one-gallon containers for approximately one year utilizing a soilless growth medium. Greenhouse temperatures were maintained at approximately 70° F. to 77° F. (21° C. to 25° C.) during the day and approximately 65° F. to 68° F. (18° C. to 20° C.) during the night.

Greenhouse light levels of 2,500 footcandles to 6,000 footcandles were maintained during the day. Measurements and numerical values represent averages of typical plants.

Botanical classification: *Heuchera×hybrida* cultivar Carnival Watermelon.

Parentage:

*Female parent*.—Proprietary *Heuchera×hybrida* breeding selection coded 222-4, not patented.

*Male parent*.—Proprietary *Heuchera×hybrida* breeding selection coded 222-9, not patented.

Propagation:

*Type*.—In vitro propagation is preferred, divisions are possible.

*Time to initiate roots in vitro*.—Approximately 10 days at 20° C.

*Time to initiate roots in greenhouse*.—Approximately 20 days at 20° C.

*Time to produce a rooted plantlet in summer*.—Approximately 42 days.

*Root description*.—Fine, fibrous; white to ivory in color.

*Rooting habit*.—Freely branching.

Plant description:

*Commercial crop time*.—Approximately 20 weeks from a rooted tissue culture plantlet to finish in a 1 gallon container.

*Growth habit and general appearance*.—Clump-forming herbaceous perennial, mounded foliage.

*Growth rate*.—Moderately vigorous.

*Outdoor plant performance*.—Use as bedding plants or in mixed-container plantings; at least tolerant to temperatures up to 35° C. and hardy to USDA zone 3.

*Size*.—Height from soil level to top of plant plane: Approximately 92.0 cm. Height from soil level to top of foliage: Approximately 25.0 cm. Width: Approximately 65.0 cm.

*Branching habit*.—No branching, basal rosettes of leaves on petioles. Number of rosettes per plant: Approximately 13.

Foliage description:

*General description*.—Moderately durable to environmental stresses. Quantity of leaves per rosette: Approximately 10. Fragrance: None. Form: Simple. Arrangement: Alternate.

*Leaves*.—Aspect: Blade is nearly perpendicular to petiole. Shape: Orbicular. Margin: Crenate, shallowly lobed. Apex: Broadly acute. Base: Cordate, sometimes moderately overlapping. Venation pattern: Palmate. Length of mature leaf: Approximately 13.0 cm. Width of mature leaf: Approximately 13.0 cm. Texture of upper surface: Dull, slightly rough, sparsely pubescent with short hairs. Texture of lower surface: Slightly glossy, moderately pubescent with short hairs. Color of upper surface of young foliage: Closest to 182C with a slight overlay of 202D and venation area and margins of 184A with 166A. Color of lower surface of young and mature foliage: N186D. Color of upper surface of mature foliage: Closest to 198D with venation area of 137A.

*Petiole*.—Length: Approximately 20.5 cm. Diameter: Approximately 3.0 mm. Texture: Sparsely pubescent with short hairs. Color: 145D with a heavy overlay of 187B.

*Stipules*.—Two leafy stipules located at the base of each petiole. Apex: Narrow acute. Length: Approximately 1.5 cm. Width: Approximately 2.0 mm. Color: 187D.

Flowering description:

*Flowering habit*.—'Carnival Watermelon' flowers once a year during late spring to midsummer under outdoor conditions.

*Lastingness of individual flower on the plant*.—Approximately 7 days.

Inflorescence description:

*General description*.—Type: Compound spike emerging from the base of the rosette with two to three cauline leaves. Fragrance: None. Length or height excluding the peduncle: Approximately 26.0 cm. Width: Approximately 10.0 cm. Quantity of inflorescences per plant: Approximately 28. Quantity of flowers per inflorescence: Approximately 76.

*Peduncle*.—Strength: Moderate. Aspect: Erect to approximately 30° angle from vertical. Length: Approximately 53.0 cm. Diameter at midpoint: Approximately 3.0 to 4.0 mm. Texture: Moderately pubescent with short hairs. Color: N137A with a heavy overlay of 187A.

Flower description:

*General description*.—Type: Single, campanulate, self-cleaning. Aspect: Drooping to slightly outward.

*Bud*.—Rate of opening: Generally takes 4 days for bud to progress from first color to fully open flower.

*Bud just before opening*.—Shape: Broadly obovate. Length: Approximately 4.0 mm. Diameter: Approximately 3.0 mm. Texture: Densely glandular pubescent. Gland Color: 187A. Color: Closest to 161D with 53B at base and tip.

*Corolla*.—Shape: Campanulate. Diameter: Approximately 5.0 mm. Depth: Approximately 6.0 mm.

*Petals*.—Quantity: 5. Arrangement: Single whorl. Shape: Narrowly elliptic. Appearance: Dull. Margin: Entire. Apex: Acute. Base: Lower half fused into hypanthium. Length: Approximately 6.0 mm. Width: Approximately 1.0 mm. Texture of upper surface: Glabrous. Texture of lower surface: Moderately glandular pubescent. Gland Color: 187A. Color of upper and lower surfaces when first and fully open: NN155D with an overlay of 77A to 77B at tip.

*Calyx*.—Shape: Campanulate. Diameter: Approximately 5.0 mm. Depth: Approximately 6.0 mm.

*Sepals*.—Quantity per flower: 5. Shape: Elliptic. Appearance: Dull. Margin of free portion: Entire. Apex: Acute. Base: Lower half fused into hypanthium. Length: Approximately 6.0 mm. Width at rim of hypanthium: Approximately 2.0 mm. Texture of upper surface: Glabrous. Texture of lower surface: Densely glandular pubescent. Gland Color: Mixture of 187A and colorless, transparent. Color of upper surface: NN155D with 184A at tip. Color of lower surface: NN155D with 161D at base and 184A at tip.

*Pedicel*.—Strength: Moderate. Aspect: The pedicel of the central flower of each spikelet is directly on top of the secondary pedicel, pedicels of secondary and tertiary flowers of each spikelet have an average 40° angle from vertical. Length: Approximately 4.0 mm. Diameter: Less than 1.0 mm. Texture: Densely glandular pubescent. Gland color: 187A. Color: N137A with a heavy overlay of 187A.

*Reproductive organs*.—Androecium: Quantity: 5 per flower. Anther shape: Ovate. Anther length: Less than 1.0 mm. Anther color: N25A. Filament length: Approximately 4.0 mm. Filament color: NN155D. Pollen amount: Moderate. Pollen color: 25C. Gynoecium: Pistil quantity: 2 per flower. Pistil length: Approximately 8.0 mm. Stigma shape: Pointed. Stigma color: NN155C. Style length: Approximately 6.0 mm. Style color: NN155C, opaque. Ovary color: NN155C with 160A at base.

Seed and fruit production: Neither seed nor fruit production has been observed.

Disease and pest resistance: Resistance to pathogens and pests common to *Heuchera* has not been observed.

What is claimed is:

1. A new and distinct cultivar of *Heuchera* plant named 'Carnival Watermelon', substantially as herein shown and described.

* * * * *